United States Patent [19]

Cesa et al.

[11] Patent Number: 4,721,803

[45] Date of Patent: Jan. 26, 1988

[54] METHOD OF MAKING A DIASTEREOMERIC MIXTURE CONTAINING TWO DIASTEREOMERIC N-ACYL-AMINO ACID ESTERS

[75] Inventors: Mark C. Cesa, South Euclid; Robert A. Dubbert, Solon; James D. Burrington, Richmond Heights, all of Ohio

[73] Assignee: The Standard Oil Company, Cleveland, Ohio

[21] Appl. No.: 792,375

[22] Filed: Oct. 29, 1985

[51] Int. Cl.[4] .................. C07C 103/46; C07D 207/16
[52] U.S. Cl. ...................................... 560/41; 548/344; 548/497; 548/533; 548/535; 560/16; 560/40; 560/153; 560/169; 560/170; 560/171; 562/443; 562/445; 562/446; 562/493; 562/557; 562/559; 562/561; 562/563; 562/567; 562/571; 562/573; 562/575; 562/590; 562/607
[58] Field of Search ...................... 560/40, 16, 41, 153, 560/169, 170, 171; 548/533, 547, 344, 497

[56] References Cited

FOREIGN PATENT DOCUMENTS 0145265 6/1985 European Pat. Off. .

OTHER PUBLICATIONS

Becker et al.; J. Org. Chem., 45 (1980), pp. 2145–2151.
Barton; "Protective Groups in Organic Chemistry" (McOmie, Ed.), Plenum Press, London (1973), pp. 46–49.

Primary Examiner—Joseph Paul Brust
Attorney, Agent, or Firm—Charles S. Lynch; John E. Miller; Larry W. Evans

[57] ABSTRACT

In the process of hydrocarboxylating an α-enamide with CO and an organic hydroxyl compound to produce a N-acyl-α-amino acid ester, the improvement comprising using as the organic hydroxyl compound reactant, an organic hydroxyl compound which has a chiral center that is essentially all L or D, thereby producing a reaction mixture having essentially no enantiomeric pairs and containing diastereomeric N-acyl-α-amino acid esters having two chiral centers.

7 Claims, No Drawings

METHOD OF MAKING A DIASTEREOMERIC MIXTURE CONTAINING TWO DIASTEREOMERIC N-ACYL-AMINO ACID ESTERS

This invention relates to a process for making an optically active mixture of an N-acyl-amino acid ester containing at least two chiral centers.

The separation of enantiomers by physical means such as fractional distillation or fractional crystallization and the like is known to be highly difficult in general.

It is an object of the invention to provide a process to produce a reaction mixture containing certain α-carboxy amides (N-acyl-amino acid esters) having two (at least) chiral centers, which mixture contains two of four possible optical configurations and contains substantially no enantiomeric pairs.

Other objects, as well as features, aspects, and advantages, of the invention will become apparent from a study of the specification, including the examples and the claims.

We have now conceived a process for making such a mixture.

Thus, in accordance with the present invention we have provided a process for making a separable reaction mixture containing diastereomeric N-acyl-α-amino acid esters having at least two chiral centers, which process comprises hydrocarboxylating an α-enamide with carbon monoxide and an organic hydroxyl compound having a chiral carbon atom, said organic hydroxyl compound being essentially only in either the l configuration or the D configuration, to produce a reaction mixture of diastereomeric N-acyl-α-amino acid esters having two chiral centers, which mixture contains essentially no enantiomeric pairs.

Further, in accordance with the present invention, there is provided a process which comprises hydrocarboxylating an α-enamide according to the equation:

to produce an essentially diastereomeric mixture of two stereoisomeric N-acyl-α-amino acid esters having at least two chiral carbons, wherein (A) the carbon bonded to $R_3$ in the product is chiral, (B) $R_3$ is not the same as $-CHR_1R_2$, $-COOR_6$, or $-N(R_4)COR_5$, (C) each of $R_1$, $R_2$, $R_3$, $R_4$, $R_5$, and $R_6$ contains no ethylenic or acetylenic unsaturation, (D) each of $R_1$, $R_2$, $R_3$, $R_4$, and $R_5$ contain zero to 15 carbon atoms and is independently selected from:

(1) H, a hydrocarbyl group, an acyl group;

(2) a hydrocarbyl group substituted with acylamino, acyl-(N-hydrocarbyl) amino, formylamino and formyl-(N-hydrocarbyl) amino, hydrocarbyloxy, hydrocarbylthio, acyloxy, acylthio, carboxyl, hydrocarbyl carboxyl, hydrocarbyl thiocarboxyl, hydrocarbyl amino, dihydrocarbyl amino, hydrocarbonyl, hydrocarbyl carbonyl, 3-indolyl, carbamoyl, hydrocarboxylcarbamoyl, dihydrocarbylcarbamoyl, 5-imidazolyl, 2-guanidinoyl and halo groups, with the proviso that (3) $R_1$ and $R_2$ can additionally be selected independently from acylamino, acyl-(N-hydrocarbyl) amino, formylamino and formyl-(N-hydrocarbyl) amino, hydrocarbyloxy, hydrocarbylthio, hydrocarbyl amino, dihydrocarbyl amino, acyloxy, acylthio, carboxyl, hydrocarbyl carboxyl, hydrocarbyl thiocarboxyl, hydrocarbonyl, hydrocarbyl carbonyl, 3-indolyl, carbamonyl, hydrocarbylcarbamoyl, dihydrocarbylcarbamoyl, 5-imidazolyl, 2-guanidinoyl and halo groups;

(E) $R_1$ and $R_2$, $R_1$ and $R_3$, or $R_2$ and $R_3$ can be linked to form a ring, and $R_4$ can be linked with $R_1$ or $R_2$ or $R_5$ to form a ring, (F) $R_6$ contains 1 to 15 carbon atoms and is independently selected from hydrocarbyl, hydrocarbyl substituted with one or more hydroxy substituents, and one of the (2) groups above, with the proviso that $R_6$ contains a chiral carbon atom.

When the $R_6OH$ reactant is essentially all L, the reaction product mixture contains the diastereomeric N-acyl-α-amino acid esters of the configurations DL and LL, where the first designation is the configuration at the alpha carbon atom and the second is the configuration of the chiral center in $R_6$. If the starting material $R_6OH$ is essentially all D optical isomer, the diastereomeric reaction product mixture contains the disetereomeric N-acyl-α-amino acid esters of the configuration DD and LD.

Specific examples of optically pure $R_6OH$ reactants useful in the present process include D- or L-3-methoxy-1 butanol, D- or L-2-octanol, L-methol, D- or L-2-butanol and L-menthoxyethanol.

In most instances $R_4$ is H or acyl in the practice of the present invention.

The process of the invention for making the diastereomeric mixture containing two (or more) stereoisomeric N-acyl-α-amino acid esters is of importance in providing a source for relatively easily obtaining a particular steroisomeric configuration of a given α-amino acid separated from any other steroisomer thereof. Thus, the mixture made according to the present invention can be resolved by ordinary measures. Thus, the two diastereomers are separated physically by well known physical means, such as fractional crystallization, fractional absorption on solid absorbents, countercurrent solvent extraction, fractional distillation where feasible, or other physical means. Thereafter, the product fractions are separately hydrolyzed in the presence of an acid or base in the conventional manner to obtain the corresponding α-amino acids and the chiral, optically active (L or D) alcohol. This is especially useful because it allows an overall process involving recycle of the chrial alcohol. Thus, in this aspect of the invention, the organic hydroxyl compound which is regenerated during the hydrolysis, is recycled at least in part to the step of hydrocarboxylating, thus allowing repeated use of $R_6OH$.

The present invention is of considerable value in providing a route for making of the L form or the D form of amino acids occurring in nature. In this aspect of the invention the product is a diastereomeric mixture containing N-acyl-α-amino acid esters that are hydrolyzable to naturally occurring amino acids. The present invention is of considerable advantage when compared to present methods. Thus, optically pure amino acids are produced industrially by the following methods:

(1) fermentation
(2) hydrolysis of plant, animal or single cell protein
(3) chemical synthesis followed by enantiomeric resolution of a subsequently prepared derivative
   (a) enzymatic enantioselective hydrolysis
   (b) chemical or physical separation of diastereomers Each of these methods has distinct disadvantages which make them costly to operate. Fermentation methods are often quite slow, require rigidly controlled conditions and highly dilute aqueous reaction media, and usually produce a mixture of products from which isolation and purification of the desired chiral amino acid is laborious and expensive. Hydrolysis of naturally occurring protein is saddled with laborious separation problems and is limited by the intrinsic concentration of the desired amino acid(s) in the protein. Chemical amino acid syntheses produce racemic mixtures of products, in addition to their use of expensive chemical feedstock such as expensive and toxic HCN.

In these syntheses the enantiomeric resolution is accomplished by derivatization of the amino acid racemic mixture, followed by enatioselective hydrolysis with an enzyme catalyst, and separation of the L-amino acid from the D-amino acid derivative, and racemization and recycle of the D-derivative (or optionally chemical hydrolysis of the D derivative when the D-amino acid is desired); or followed by physical separation when the derivatization is performed with a chiral reagent. These procedures add steps to the overall processes and are expensive and time and labor consuming.

Among the advantages of the present invention are:
(1) Lower cost starting materials;
(2) Initial formation of diastereomeric products as a result of the amino acid forming reaction, not a subsequent step:
(3) Fewer process steps.

In a particularly advantageous aspect of the invention we have provided a process which comprises (1) hydrocarboxylating an α-enamide with carbon monoxide and an organic hydroxyl compound having a chiral carbon atom, said organic hydroxyl compound being essentially only in either the L configuration or the D configuration to produce a reaction mixture of diastereomeric N-acyl-α-amino acid esters having two chiral centers, which mixture contains essentially no enantiomeric pairs, (2) separating the diastereomers by physical means, (3) hydrolyzing each diastereomer to make the L and D α-amino acids, plus said organic hydroxyl compound, and (4) recycling at least a part of said hydroxyl compound to step (1).

In European patent application No. 84 307,683.7, published June 19, 1985, under Publication No. 0145,265, is disclosed the details of how to hydrocarboxylate alpha enamides with carbon monoxide and an organic hydroxyl compound. Reference is made to this document for the details of carrying out the hydrocarboxylation, and the disclosures of this European patent application in this regard are incorporated herein by reference.

It should be noted that in such a hydrocarboxylation, the alpha carbon atom in the hydrocarboxylation product is chiral. Therefore, the N-acyl-α-amino acid ester produced is a racemic mixture of the L and D forms. If one wants either the L form or the D form without its enantiomer, the separation is difficult and expensive.

The crux of the broadest aspect of the present invention is the concept of employing an organic hydroxyl compound starting material in the foregoing reaction that is essentially all L or all D so that when the reaction is carried out, the product will contain essentially no enantiomeric pairs, as previously discussed. Since the product mixture has no enantiomeric pairs, the stereoisomers can be more easily separated by physical means than can a reaction mixture containing enantiomeric pairs.

The diastereomeric N-acyl-α-amino acid ester mixtures of the invention are all useful, as noted, to make optically active α-amino acids by hydrolysis. The amino acids are all useful to make peptides by known methods, and these can be converted to proteins to make animal feed supplements, for instance. The amino acids can also be converted to useful solid polyamides by conventional condensation techniques, useful for thermoplastic molding of solid shapes, such as structural parts, plates, tumblers, etc.

The hydrocarboxylation reaction is carried out catalytically and can be effected continuously or in a batch operation in the liquid phase, or in the vapor phase where feasible at the reaction temperatures noted hereafter. Usually it is effected in a batch operation in a solvent under pressure.

The reactant concentrations can vary widely and are not critical. For convenience, the ratio of the hydrocarboxylation reactant $R_6OH$ to the enamide should be no greater than 10/1 on a molar basis and is preferably at least 1/1. The amount of carbon monoxide can vary widely, but it is usual to carry out the reaction under a carbon monoxide pressure of zero to 3500 psig, more usually 250 to 2500 psig. The amount of catalyst can also vary widely. Most conveniently, the amount of catalyst is between 0.001 and 100 mole percent based on the enamide, more usually 0.1 to 10 mole percent.

Usually, the reaction is carried out with a solvent. The solvent should be inert under the reaction conditions and preferably dissolve the active catalyst species as well as the reactants but not necessarily all of the CO. Suitable solvents found to date include tetrahydrofuran, benzene, $CH_3CN$ and $CH_2Cl_2$, $CHCl_3$, $CH_3Cl$, $CCl_4$, toluene, ethyl ether and dimethylformamide. The now preferred solvent is tetrahydrofuran, particularly when using $(\phi_3P)_2PdCl_2$ catalyst, or other palladium compounds. Usually, the amount of solvent in the system will be such that the enamide concentration is at least about 0.01 weight percent in the solution, but not over 70 weight percent.

The reaction is normally carried out at a temperature of 0° to 250° C., preferably 20° to 150° C. However, the reaction temperature can be below or above this if desired. Reaction times on the order of 0.1 to 250 hours can be employed, with reaction times on the order of 2 to 100 hours being more convenient.

Catalysts useful in the hydrocarboxylation reaction are generally transition metal catalyst compounds, particularly coordination complexes of such metals. Palladium coordination complexes are effective, especially those complexed with phosphine such as $P\phi_3$. Cobalt coordination complexes are also effective, such as $Co_2(CO)_8$ and its phosphine- or phosphite-substituted derivatives. When Co complexes are used it is advantageous to incorporate hydrogen and a tertiary amine, pyridine or a pyridine derivative into the reaction mixture to enhance catalytic activity.

Once the hydrocarboxylation reaction is completed, the product N-acyl-α-amino acid ester diastereomers can be recovered from the reaction system in a conventional manner, such as for example, by vacuum distillation or crystallization.

As noted, the optically active α-amino acids have numerous uses. The naturally occurring amino acids have known uses. In particular, phenylalanine can be used to make the sweetner aspartame in a known manner. See U.S. Pat. No. 3,492, 131, issued Jan. 27, 1970.

The following examples are illustrative only and are not to be considered in any way limiting.

EXAMPLE 1

A 70 mL stainless steel high pressure reactor fitted with a Pyrex glass liner and magnetic stir bar is charged with THF (5 mL), L-3-methoxy-1-butanol (0.5 mmol), (PPh$_3$)$_2$PdCl$_2$ (36 mg, 0.05 mmol), and N-$\beta$-styrylbenzamide (0.5 mmol). The reactor is sealed, pressurized to 1000 psig with CO, and stirred for 24 hours at 100° C. The product mixture, isolated after removal of gas from the reactor vessel, contains a mixture of two diastereomeric phenylalanine derivatives, N-benzoyl-L-phenylalanine L-3-methoxy-1-butyl ester and N-benzoyl-D-phenylalanine L-3-methoxy-1-butyl ester. These diastereomers are separated by column chromatography on silica gel with benzene-ethyl acetate eluent and are separately hydrolyzed by heating to 100° C. in 1N HCl for 2 hours to give pure L- and D-phenylalanine, benzoic acid, and L-3-methoxy-1-butanol, which is thereafter recycled to a repeat of the foregoing hydrocarboxylation reaction.

EXAMPLE 2

A 70 mL stainless steel high pressure reactor fitted with a Pyrex glass liner and magnetic stir bar is charged with THF (5 mL), L-2-octanol (0.5 mmol), Co$_2$(CO)$_8$ (0.05 mmol), pyridine (0.25 mmol), and N-acetyl-2-pyrroline (0.5 mmol). The reactor is sealed, pressurized to 1500 psig with 15:1 CO:H$_2$ and stirred for 24 hours at 100° C. The product mixture, isolated after removal of gas from the reactor vessel, contains a mixture of two diastereomeric proline derivatives, N-acetyl-L-proline L-2-octyl ester and N-acetyl-D-proline L-2-octyl ester. These diastereomers are separated by column chromatography on silica gel with benzene-ethyl acetate eluent and are separately hydrolyzed by heating to 100° C. in 1N HCl for 2 hours to give pure L- and D-proline, acetic acid, and L-2-octanol, which is thereafter recycled to a repeat of the foregoing hydrocarboxylation reaction.

EXAMPLE 3

0.10 mol of isobutyraldehyde and 0.20 mol of benzamide are heated together at 100° C. with stirring, and the product solid is heated in a sublimator at 250° C. and 1 mm Hg until formation of the enamide 1-benzoylamino-2-methylpropene is complete. A 70 mL stainless steel high pressure reactor fitted with a Pyrex glass liner and magnetic stir bar is charged with THF (5 mL), L-menthol (0.5 mmol), Co$_2$(CO)$_8$ (0.05 mmol), pyridine (0.25 mmol), and 1-benzoylamino-2-methylpropene (0.5 mmol). The reactor is sealed, pressurized to 1500 psig with 15:1 CO:H$_2$ and stirred for 24 hours at 100° C. The product mixture, isolated after removal of gas from the reactor vessel, contains a mixture of two diastereomeric valine derivatives, N-benzoyl-L-valine L-menthyl ester and N-benzoyl-D-valine L-menthyl ester. These diastereomers are separated by column chromatography on silica gel with benzene-ethyl acetate eluent and are separately hydrolyzed by heating to 100° C. in 1N HCl for 2 hours to give pure L- and D-valine, benzoic acid, and L-menthol, which is thereafter recycled to a repeat of the foregoing hydrocarboxylation reaction.

EXAMPLE 4

A 70 mL stainless steel high pressure reactor fitted with a Pyrex glass liner and magnetic stir bar is charged with THF (5 mL), L-menthoxyethanol (0.5 mmol), Co$_2$(CO)$_8$ (0.05 mmol), pyridine (0.25 mmol), and N-vinylsuccinimide (0.5 mmol). The reactor is sealed, pressurized to 1500 psig with 15:1 CO:H$_2$, and stirred for 24 hours at 100° C. The product mixture, isolated after removal of gas from the reactor vessel, contains a mixture of two diastereomeric alanine derivatives, N-succinyl-L-alanine L-menthoxyethyl ester and N-succinyl-D-alanine L-menthoxyethyl ester. These diastereomers are separated by column chromatography on silica gel with benzene-ethyl acetate eluent and are separately hydrolyzed by heating to 100° C. in 1N HCl for 2 hours to give pure L- and D-alanine, succinic acid, and L-menthoxyethanol, which is thereafter recycled to a repeat of the foregoing hydrocarboxylation reaction.

EXAMPLE 5

0.10 mol of isovaleraldehyde and 0.20 mol of succinimide are heated together at 100° C. with stirring, and the product solid is heated in a sublimator at 250° C. and 1 mm Hg until formation of the enamide 1-succinimido-3-methyl-1-butene is complete. A 70 mL stainless steel high pressure reactor fitted with a Pyrex glass liner and magnetic stir bar is charged with THF (5 mL), L-2-butanol (0.5 mmol), Co$_2$(CO)$_8$ (0.05 mmol), pyridine (0.25 mmol), and 1-succinimido-3-methyl-1-butene (0.5 mmol). The reactor is sealed, pressurized to 1500 psig with 15:1 CO:H$_2$, and stirred for 24 hours at 100° C. The product mixture, isolated after removal of gas from the reactor vessel, contains a mixture of two diastereomeric leucine derivatives, N-succinyl-L-leucine L-2-butyl ester and N-succinyl-D-leucine L-2-butyl ester. These diastereomers are separated by column chromatography on silica gel with benzene-ethyl acetate eluent and are separately hydrolyzed by heating to 100° C. in 1N HCl for 2 hours to give pure L- and D-leucine, succinic acid, and L-2-butanol, which is thereafter recycled to a repeat of the foregoing hydrocarboxylation reaction.

EXAMPLE 6

0.10 mol of methoxyacetaldehyde and 0.20 mol of acetamide are heated together at 100° C. with stirring, and the product solid is heated in a sublimator at 250° C. and 1 mm Hg until formation of the enamide 1-acetamido-2-methoxyethylene is complete. A 70 mL stainless steel high pressure reactor fitted with a Pyrex glass liner and magnetic stir bar is charged with THF (5 mL), D-3-methoxy-1-butanol (0.5 mmol), (PPh$_3$)$_2$PdCl$_2$ (36 mg, 0.05 mmol), and 1-acetamido-2-methoxyethylene (0.5 mmol). The reactor is sealed, pressurized to 1000 psig with CO, and stirred for 24 hours at 100° C. The product mixture, isolated after removal of gas from the reactor vessel, contains a mixture of two diastereomeric serine derivatives, N-acetyl-L-serine D-3-methoxy-1-butyl ester and N-acetyl-D-serine D-3-methoxy-1-butyl ester. These diastereomers are separated by column chromatography on silica gel with benzene-ethyl acetate eluent and are separately hydrolyzed by heating to 100° C. in 1N HCl for 2 hours to give pure L- and D-serine, acetic acid, and D-3-methoxy-1-butanol, which is thereafter recycled to a repeat of the foregoing hydrocarboxylation reaction.

EXAMPLE 7

0.10 mol of 3-(D-2-octyloxycarbonyl)acetaldehyde and 0.20 mol of acetamide are heated together at 100° C. with stirring, and the product solid is heated in a sublimator at 250° C. and 1 mm Hg until formation of the enamide D-2-octyl-2-acetamidoacrylate is complete. A 70 mL stainless steel high pressure reactor fitted with a Pyrex glass liner and magnetic stir bar is charged with THF (5 mL), D-2-octanol (0.5 mmol), (PPh$_3$)$_2$PdCl$_2$ (36 mg, 0.05 mmol), and D-2-octyl-2-acetamidoacrylate (0.5 mmol). The reactor is sealed, pressurized to 1000 psig with CO, and stirred for 24 hours at 100° C. The product mixture, isolated after removal of gas from the reactor vessel, contains a mixture of two diastereomeric aspartic acid derivatives, N-acetyl-L-aspartic acid di (D-2-octyl) ester and N-acetyl-D-aspartic acid di (D-2-octyl) ester. These diastereomers are separated by column chromatography on silica gel with benzene-ethyl acetate eluent and are separately hydrolyzed by heating to 100° C. in 1N HCl for 2 hours to give pure L- and D-aspartic acid, acetic acid, and D-2-octanol, which is thereafter recycled to a repeat of the foregoing hydrocarboxylation reaction.

EXAMPLE 8

0.10 mol of 2-(benzylthio)acetaldehyde and 0.20 mol of acetamide are heated together at 100° C. with stirring, and the product solid is heated in a sublimator at 250° C. and 1 mm Hg until formation of the enamide 1-acetamido-2-benzylthioethene is complete. A 70 mL stainless steel high pressure reactor fitted with a Pyrex glass liner and magnetic stir bar is charged with THF (5 mL), D-menthol (0.5 mmol), (PPh$_3$)$_2$PdCl$_2$ (36 mg, 0.05 mmol), and 1-acetamido-2-benzylthioethene (0.5 mmol). The reactor is sealed, pressurized to 1000 psig with CO, and stirred for 24 hours at 100° C. The product mixture, isolated after removal of gas from the reactor vessel, contains a mixture of two diastereomeric cysteine derivatives, N-acetyl-L-benzylcysteine D-menthyl ester and N-acetyl-D-benzylcysteine D-menthyl ester. These diastereomers are separated by column chromatography on silica gel with benzene-ethyl acetate eluent and are separately hydrolyzed by heating to 100° C. in 1N HCl for 2 hours to give pure L- and D-cysteine, benzyl alcohol, acetic acid, and D-menthol, which is thereafter recycled to a repeat of the foregoing hydrocarboxylation reaction.

EXAMPLE 9

0.10 mol of 3-(D-2-butoxycarbonyl)propionaldehyde and 0.20 mol of acetamide are heated together at 100° C. with stirring, and the product solid is heated in a sublimator at 250° C. and 1 mm Hg until formation of the enamide 1-acetamido-3-(D-2-butoxycarbonyl)propene is complete. A 70 mL stainless steel high pressure reactor fitted with a Pyrex glass liner and magnetic stir bar is charged with THF (5 mL), D-2-butanol (0.5 mmol), (PPh$_3$)$_2$PdCl$_2$ (36 mg, 0.05 mmol), and 1-acetamido-3-(D-2-butoxycarbonyl)propene (0.5 mmol). The reactor is sealed, pressurized to 1000 psig with CO, and stirred for 24 hours at 100° C. The product mixture, isolated after removal of gas from the reactor vessel, contains a mixture of two diastereomeric glutamic acid derivatives, N-acetyl-L-glutamic acid di(D-2-butyl) ester and N-acetyl-D-glutamic acid di(D-2-butyl) ester. These diastereomers are separated by column chromatography on silica gel with benzene-ethyl acetate eluent and are separately hydrolyzed by heating to 100° C. in 1N HCl for 2 hours to give pure L- and D-glutamic acid, acetic acid, and D-2-butanol, which is thereafter recycled to a repeat of the foregoing hydrocarboxylation reaction.

EXAMPLE 10

0.10 mol of 4-oxobutyraldehyde and 0.20 mol of acetamide are heated together at 100° C. with stirring, and the product solid is heated in a sublimator at 250° C. and 1 mm Hg until formation of the enamide 1-acetamido-3-carbamoylpropene is complete. A 70 mL stainless steel high pressure reactor fitted with a Pyrex glass liner and magnetic stir bar is charged with THF (5 mL), L-menthoxyethanol (0.5 mmol), (PPh$_3$)$_2$PdCl$_2$ (36 mg, 0.05 mmol, and 1-acetamido-3-carbamoylpropene (0.5 mmol). The reactor is sealed, pressurized to 1000 psig with CO, and stirred for 24 hours at 100° C. The product mixture, isolated after removal of gas from the reactor vessel, contains a mixture of two diastereomeric tryptophan derivatives, N-acetyl-L-tryptophan L-menthoxyethyl ester and N-acetyl-D-glutamine L-menthoxyethyl ester. These diastereomers are separated by column chromatography on silica gel with benzene-ethyl acetate eluent and are separately hydrolyzed by heating to 100° C. in 1N HCl for 2 hours to give pure L- and D-glutamine, acetic acid, and L-menthoxyethanol, which is thereafter recycled to a repeat of the foregoing hydrocarboxylation reaction.

EXAMPLE 11

0.10 mol of imidazole-4-acetaldehyde and 0.20 mol of acetamide are heated together at 100° C. with stirring, and the product solid is heated in a sublimator at 250° C. and 1 mm Hg until formation of the enamide 1-acetamido-2-(4-imidazolyl)ethene is complete. A 70 mL stainless steel high pressure reactor fitted with a Pyrex glass liner and magnetic stir bar is charged with THF (5 mL), L-2-butanol (0.5 mmol), (PPh$_3$)$_2$PdCl$_2$ (36 mg, 0.05 mmol), and 1-acetamido-2-(4-imidazolyl)ethene (0.5 mmol). The reactor is sealed, pressurized to 1000 psig with CO, and stirred for 24 hours at 100° C. The product mixture, isolated after removal of gas from the reactor vessel, contains a mixture of two diastereomeric histidine derivatives, N-acetyl-L-histidine L-2-butyl ester and N-acetyl-D-histidine L-2-butyl ester. These diastereomers are separated by column chromatography on silica gel with benzene-ethyl acetate eluent and are separately hydrolyzed by heating to 100° C. in 1N HCl for 2 hours to give pure L- and D-histidine, acetic acid, and L-2-butanol, which is thereafter recycled to a repeat of the foregoing hydrocarboxylation reaction.

0.10 mol of 3-methylthiopropanal and 0.20 mol of acetamide are heated together at 100° C. with stirring, and the product solid is heated in a sublimator at 250° C. and 1 mm Hg until formation of the enamide 1-acetamido-3-methylthiopropene is complete. A 70 mL stainless steel high pressure reactor fitted with a Pyrex glass liner and magnetic stir bar is charged with THF (5 mL), L-3-methoxy-1-butanol (0.5 mmol), (PPh$_3$)$_2$PdCl$_2$ (36 mg, 0.05 mmol), and 1-acetamido-3-methylthiopropene (0.5 mmol). The reactor is sealed, pressurized to 1000 psig with CO, and stirred for 24 hours at 100° C. The product mixture, isolated after removal of gas from the reactor vessel, contains a mixture of two diastereomeric methionine derivatives, N-acetyl-L-methionine L-3-methoxy-1-butyl ester and N-acetyl-D-methionine L-3-methoxy-1-butyl ester. These diastereomers are separated by column chromatography on silica gel with benzene-ethyl acetate eluent and are separately hydrolyzed by heating to 100° C. in 1N HCl for 2 hours to give pure L- and D-methionine, acetic acid, and L-3- methoxy-1-butanol, which is thereafter recycled to a repeat of the foregoing hydrocarboxylation reaction.

EXAMPLE 13

0.10 mol of indole-3-acetaldehyde and 0.20 mol of acetamide are heated together at 100° C. with stirring, and the product solid is heated in a sublimator at 250° C. and 1 mm Hg until formation of the enamide 1-acetamido-2-(3-indolyl)ethene is complete. A 70 mL stainless steel high pressure reactor fitted with a Pyrex glass liner and magnetic stir bar is charged with THF (5 mL), L-menthoxyethanol (0.5 mmol), $(PPh_3)_2PdCl_2$ (36 mg, 0.05 mmol), and 1-acetamido-2-(3-indolyl)ethene (0.5 mmol). The reactor is sealed, pressurized to 1000 psig with CO, and stirred for 24 hours at 100° C. The product mixture, isolated after removal of gas from the reactor vessel, contains a mixture of two diastereomeric tryptophan derivatives, N-acetyl-L-tryptophan L-menthoxyethyl ester and N-acetyl-D-tryptophan L-menthoxyethyl ester. These diastereomers are separated by column chromatography on silica gel with benzene-ethyl acetate eluent and are separately hydrolyzed by heating to 100° C. in 1N HCl for 2 hours to give pure L- and D-tryptophan, acetic acid, and L-menthoxyethanol, which is thereafter recycled to a repeat of the foregoing hydrocarboxylation reaction.

EXAMPLE 14

0.10 mol of p-methoxyphenylacetaldehyde and 0.20 mol of acetamide are heated together at 100° C. with stirring, and the product solid is heated in a sublimator at 250° C. and 1 mm Hg until formation of the enamide 1-acetamido-2-(4-methoxyphenyl) ethene is complete. A 70 mL stainless steel high pressure reactor fitted with a Pyrex glass liner and magnetic stir bar is charged with THF (5 mL), L-2-octanol, (0.5 mmol), $(PPh_3)_2PdCl_2$ (36 mg, 0.05 mmol, and 1-acetamido-2-(4-methoxyphenyl)ethene (0.5 mmol). The reactor is sealed, pressurized to 1000 psig with CO, and stirred for 24 hours at 100° C. The product mixture, isolated after removal of gas from the reactor vessel, contains a mixture of two diastereomeric tyrosine derivatives, N-acetyl-L-O-methyltyrosine L-2-octyl ester and N-acetyl-D-O-methyltyrosine L-2-octyl ester. These diastereomers are separated by column chromatography on silica gel with benzene-ethyl acetate eluent and are separately hydrolyzed by heating to 100° C. in 1N HCl for 2 hours to give pure L- and D-tyrosine, methanol, acetic acid, and L-2-octanol, which is thereafter recycled to a repeat of the foregoing hydrocarboxylation reaction.

EXAMPLE 15

0.10 mol of 3,4-diacetyloxyphenylacetaldehyde and 0.20 mol of acetamide are heated together at 100° C. with stirring, and the product solid is heated in a sublimator at 250° C. and 1 mm Hg until formation of the enamide 1-acetamido-2-(3,4-diacetyloxyphenyl)ethene is complete. A 70 mL stainless steel high pressure reactor fitted with a Pyrex glass liner and magnetic stir bar is charged with THF (5 mL), L-menthoxyethanol (0.5 mmol), $(PPh_3)_2PdCl_2$ (36 mg, 0.05 mmol), and 1-acetamido-2-(3,4-diacetyloxyphenyl)ethene (0.5 mmol). The reactor is sealed, pressurized to 1000 psig with CO, and stirred for 24 hours at 100° C. The product mixture, isolated after removal of gas from the reactor vessel, contains a mixture of two diastereomeric dopa derivatives, O,O',N-triacetyl-L-dopa L-menthoxyethyl ester and O,O',N-triacetyl-D-dopa L-menthoxyacetyl ester. These diastereomers are separated by column chromatography on silica gel with benzene-ethyl acetate eluent and are separately hydrolyzed by heating to 100° C. in 1N HCl for 2 hours to give pure L- and D-dopa, acetic acid, and L-menthoxyethanol, which is thereafter recycled to a repeat of the foregoing hydrocarboxylation reaction.

EXAMPLE 16

0.10 mol of 4-acetamidobutyraldehyde and 0.20 mol of acetamide are heated together at 100° C. with stirring, and the product solid is heated in a sublimator at 250° C. and 1 mm Hg until formation of the enamide 1,4-diacetamido-1-butene is complete. A 70 mL stainless steel high pressure reactor fitted with a Pyrex glass liner and magnetic stir bar is charged with THF (5 mL), L-3-methoxy-1-butanol (0.5 mmol), $(PPh_3)_2PdCl_2$ (36 mg, 0.05 mmol), and 1,4-diacetamido-1-butene (0.5 mmol). The reactor is sealed, pressurized to 1000 psig with CO, and stirred for 24 hours at 100° C. The product mixture, isolated after removal of gas from the reactor vessel, contains a mixture of two diastereomeric ornithine derivatives, N,N'-diacetyl-L-ornithine L-3-methoxy-1-butyl ester and N,N'-diacetyl-D-ornithine L-3-methoxy-1-butyl ester. These diastereomers are separated by column chromatography on silica gel with benzene-ethyl acetate eluent and are separately hydrolyzed by heating to 100° C. in 1N HCl for 2 hours to give pure L- and D-ornithine, acetic acid, and L-3-methoxy-1-butanol, which is thereafter recycled to a repeat of the foregoing hydrocarboxylation reaction.

As used herein the term "hydroxyl" in the phrase "organic hydroxyl compound" excludes the hydroxyl group of a carboxylic acid group. —COOH.

As will be evident to those skilled in the art, various modifications of this invention can be made or followed in the light of the foregoing disclosure and discussion without departing from the spirit and scope of the disclosure or from the scope of the claims.

We claim:

1. In the process of hydrocarboxylating an α-enamide with CO and an organic hydroxyl compound to produce a N-acyl-α-amino acid ester whose alpha C atom is chiral, the improvement comprising using as the organic hydroxyl compound reactant, an organic hydroxyl compound which also has a chiral C atom that is essentially all L or D, thereby producing a reation mixture having essentially no enantiomeric pairs and containing diastereomeric N-acyl-α-amino acid esters having two chiral centers, said hydrocarboxylating simultaneously creating (1) said ester, the chirality of said alpha C atom in L, D form and (2) the second chiral center in said ester in essentially all L or all D form.

2. A process which comprises (1) making an N-acyl-α-amino acid ester whose alpha C atom and another C atom are chiral, by hydrocarboxylating an α-enamide with carbon monoxide and an organic hydroxyl compound having a chiral carbon atom, said organic hydroxyl compound being essentially only in either the L configuration or the D configuration, to produce a reaction mixture of diastereomeric N-acyl-α-amino acid esters having two chiral centers, which mixture contains essentially no enantiomeric pairs, (2) separating the diastereomers by physical means, (3) hydrolyzing each diastereomer to make the L and D α-amino acids plus organic hydroxyl compound, and (4) recycling at least a part of said hydroxyl compound to step (1).

3. In a process which comprises making an essentially enantiomerically pure L or D α-amino acid which comprises hydrocarboxylating an α-enamide with CO and an organic hydroxyl compound to produce a N-acyl-α-amino acid ester whose alpha C atom is chiral, the improvement comprising using as the organic hydroxyl compound reactant, an organic hydroxyl compound which also has a chiral C atom that is essentially all L or D, thereby producing a reaction mixture having essentially no enantiomeric pairs and containing diastereomeric N-acyl-α-amino acid esters having two chiral centers, separating the diastereomers by physical means, and thereafter hydrolyzing at least one of said diastereomers to make at least the L or the D α-amino acid in essentially enantiomerically pure form, said hydrocarboxylating simultaneously creating (1) said ester, the chirality of said alpha C atom in L, D form and (2) the second chiral center in said ester in essentially all L or all D form.

4. A process according to claim 1 wherein said α-enamide is N-β-styrylbenzamide.

5. A process according to claim 4 wherein said organic hydroxyl compound is L-3-methoxy-1-butanol.

6. A process according to claim 3 wherein said α-enamide is N-β-styrylbenzamide.

7. A process according to claim 6 wherein said organic hydroxyl compound is L-3-methoxy-1-butanol.

* * * * *